US009239226B2

(12) United States Patent
Fedosejevs et al.

(10) Patent No.: US 9,239,226 B2
(45) Date of Patent: Jan. 19, 2016

(54) APPARATUS AND METHOD FOR MEASURING THE QUANTITY AND OPTICAL PARAMETERS OF A LIQUID IN A CONTAINER USING THE PRINCIPLE OF OPTICAL LOW COHERENCE REFLECTOMETRY

(71) Applicant: The Governors of the University of Alberta, Edmonton (CA)

(72) Inventors: Robert Fedosejevs, Edmonton (CA); Ilya Utkin, Edmonton (CA); Sunita Sindhu, Edmonton (CA); Ying Yin Tsui, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 17 days.

(21) Appl. No.: 14/162,390

(22) Filed: Jan. 23, 2014

(65) Prior Publication Data
US 2014/0204390 A1    Jul. 24, 2014

Related U.S. Application Data

(60) Provisional application No. 61/755,737, filed on Jan. 23, 2013.

(51) Int. Cl.
*G01B 9/02* (2006.01)
*G01B 11/06* (2006.01)
*G01N 21/45* (2006.01)

(52) U.S. Cl.
CPC .......... *G01B 9/0209* (2013.01); *G01B 11/0625* (2013.01); *G01B 11/0675* (2013.01); *G01N 21/45* (2013.01)

(58) Field of Classification Search
CPC .......... G01N 21/45; G01N 2035/1025; G01B 9/0209; G01F 23/00; G01F 23/284; G01F 23/292; G01F 23/2921; G01F 23/2928
See application file for complete search history.

(56) References Cited

U.S. PATENT DOCUMENTS

| | | | | |
|---|---|---|---|---|
| 5,257,090 A | * | 10/1993 | Meinzer et al. | 356/498 |
| 5,659,392 A | * | 8/1997 | Marcus et al. | 356/497 |
| 6,229,476 B1 | * | 5/2001 | Lutke et al. | 342/124 |
| 7,636,166 B2 | * | 12/2009 | De Groot et al. | 356/500 |
| 7,855,790 B2 | * | 12/2010 | Nishizawa et al. | 356/497 |
| 8,451,452 B2 | * | 5/2013 | Podoleanu et al. | 356/479 |
| 8,825,434 B2 | * | 9/2014 | Koshimizu et al. | 702/134 |
| 2009/0128395 A1 | * | 5/2009 | Baath | 342/124 |
| 2012/0268578 A1 | * | 10/2012 | Vertikov et al. | 348/65 |

* cited by examiner

*Primary Examiner* — Gregory J Toatley
*Assistant Examiner* — Shawn Decenzo
(74) *Attorney, Agent, or Firm* — LeClairRyan, a Professional Corporation

(57) ABSTRACT

An apparatus for measuring the quantity and optical parameters of a liquid in a container using the principle of optical low coherence reflectometry is provided, the apparatus having: a source arm with a low coherence light source; a reference arm including a reference lens, a mirror, means for adjusting the distance between the reference lens and the mirror and means for measuring the distance between the reference lens and the mirror; a test arm with a test lens; means for dividing the output of the source arm between the test arm and the reference arm; means for combining light reflected back into the reference arm and the test arm to create an interference signal; and means for detecting and analyzing the interference signal.

8 Claims, 5 Drawing Sheets

APPARATUS AND METHOD FOR MEASURING THE QUANTITY AND OPTICAL PARAMETERS OF A LIQUID IN A CONTAINER USING THE PRINCIPLE OF OPTICAL LOW COHERENCE REFLECTOMETRY

RELATED APPLICATIONS

This application claims the benefit of U.S. Provisional Patent Application No. 61/755,737 which is hereby incorporated by reference.

FIELD OF THE INVENTION

The present disclosure is related to the field of optical measuring techniques, in particular, optical measuring techniques for measuring the thickness and refractive index of liquid layers.

BACKGROUND OF THE INVENTION

Interferometry refers to the superposition of electromagnetic waves in order to extract information about those waves. Low-coherence interferometry (LCI) is an interferometry technique utilizing low-coherence light sources. LCI allows for precise measurement of the amplitude and the relative phase of reflected or backscattered light.

One common type of interferometer is a Michelson optical interferometer. Michelson interferometers have a light source, a beam splitter which splits the light into a reference arm and a measurement arm and a light detector. The measurement beam is reflected from the specimen being analyzed. The time required for the measurement beam to travel back along the measurement arm and arrive at the light detector depends on the various refractive indexes in the different layers of the specimen. The reference mirror is positioned on a movable delay line to allow the time delay of the reference arm to be adjusted and matched to the time delay of the light reflecting off of the specimen and travelling through the measurement arm. The light from the reference mirror and the light from the specimen, which have multiple partial reflections at multiple delay times, are then recombined and detected. The optical distance of the reflecting regions in the specimen are determined by analyzing the recombined light beam as detected by the light detector.

Optical low-coherence reflectometry (OLCR) is an interferometry technique for one-dimensional optical ranging where the amplitude and longitudinal delay of backscattering from a specimen are resolved using a Michelson interferometer incorporating a low-coherence light source. This technique can resolve surfaces spaced by less than 10 µm and can detect optical power reflectivities as low as −136 dB. OLCR Michelson interferometers can be constructed using fiber optic components, thus minimizing their size and weight, and lowering the requirements for the alignment.

Referring to FIG. 1, an example of a basic OLCR interferometer is shown. Such an interferometer includes: a low-coherence source (A); a source-to-isolator fiber (B); an isolator (C); an isolator output fiber (D); a fiber coupler (E); a test arm fiber (F); a reference arm fiber (I); a mirror (H); a detector fiber (J); and a light detector (K). Light travels from the low-coherence source (A) through the source-to-isolator fiber (B), the isolator (C) and the isolator output fiber (D) to the fiber coupler (E), which splits the beam between the test arm fiber (F) and the reference arm fiber (I). Light in the test arm fiber (F) travels to the specimen (G), and is reflected back through the test arm fiber (F). Light in the reference arm fiber (I) travels to the mirror (H) and is reflected back through the reference arm fiber (I). The reflected light from the test arm fiber (F) and the reflected light from the reference arm fiber (I) are recombined in the fiber coupler (E). The recombined light travels through the detector fiber (J) to the detector (K). The isolator (C) prevents reflected light from interfering with light from the source (A). When the optical path length to the mirror (H) is equal to the optical path length to a reflection in the specimen (G), the reflected light from the test arm (F) and the reflected light from the reference arm (I) add coherently to produce coherence fringes (known as coherence spikes) at the light detector (K). To improve the detection of the coherence signal, the reference arm (I) can include a phase modulation device. In some embodiments, the phase modulation device has a vibrating mirror; in other embodiments, the phase modulation device has an electro-optic phase modulator. The amplitude of the coherence signal is a function of the reflection coefficient of the specimen (G). In some embodiments, the amplitude of the coherence signal can be proportional to the square root of the product of the powers in the reference and signal channels. Thus, translating the mirror (H) to vary the optical path length of the reference arm (I) allows the reflectivity profile of the specimen (G) to be mapped. When the optical path length difference is larger than the coherence length of the source (A), the coherence signal no longer exists. The coherence length of a source $L_c$ is determined by the following equation:

$$L_c = \frac{\lambda^2}{n\Delta\lambda}$$

In this equation, n is the refractive index of the test material, $\lambda$ is the average source wavelength, and $\Delta\lambda$ is the source spectral width.

One potential application for OLCR is in the field of hydrocarbon condensation measurement systems used in the oil and gas industry. These systems must be capable of accurately quantifying small amounts of liquids under extreme temperatures and pressures. For the purposes of chemical analysis, it is also desirable that such systems be capable of accurately measuring the refractive indices of liquids.

Fiber optic systems have a number of advantages over other types of prior art liquid measurement systems, including immunity to electromagnetic interference, the ability to operate in a wide variety of environmental conditions, high sensitivity and the potential for multiplexing.

Current fiber optic liquid measurement systems are often complex and sensitive to external disturbances. Many of these systems are designed to measure only the refractive indices of test liquids and are not capable of measuring the thickness of a liquid layer. Furthermore, they require a fiber tip to be inserted into the test liquid.

Current fiber optic liquid measurement systems capable of measuring the thickness of a liquid layer require an optical reflecting surface separate from and behind the test liquid. Such systems also require a large lens surface to collect the light reflected from the test liquid.

It is therefore desirable to provide an apparatus and method for measuring the quantity and optical parameters of a liquid in a container using the principle of optical low coherence reflectometry that overcomes the shortcomings of the prior art.

SUMMARY OF THE INVENTION

An apparatus for measuring the quantity and optical parameters of a liquid in a container using the principle of optical low coherence reflectometry is provided. In some embodiments, the apparatus includes: a source arm having a low coherence light source; a reference arm with a reference lens, a mirror, means for adjusting the distance between the reference lens and the mirror and means for measuring the distance between the reference lens and the mirror; a test arm with a test lens; means for dividing the output of the source arm between the test arm and the reference arm; means for combining light reflected back into the reference arm and the test arm to create an interference signal; and means for detecting and analyzing the interference signal.

In some embodiments, the source arm has an isolator to prevent feedback from the reference arm and the test arm from entering the source arm.

In some embodiments, the low coherence light source includes an Erbium-doped fiber amplifier.

In some embodiments, the reference arm includes a phase modulator.

In some embodiments, the phase modulator includes a function generator and means for oscillating the mirror in accordance with the output of the function generator, with the function generator used to trigger the means for detecting and analyzing the interference signal.

In some embodiments, the test lens can be a gradient-index lens.

In some embodiments, the means for detecting and analyzing the interference signal includes a photodiode, an operational amplifier circuit, an analog-to-digital converter and a computer.

In some embodiments, the source arm, the reference arm, the test arm, the means for dividing the output of the source arm between the test arm and the reference arm and the means for combining light reflected back into the reference arm and the test arm to create an interference signal all include fiber optic components.

A method for calculating the thickness t and refractive index n of a liquid in a container is provided. In some embodiments, the method includes: providing an apparatus for measuring the quantity and optical parameters of a liquid in a container using the principle of optical low coherence reflectometry, the apparatus including a source arm having a low coherence light source; a reference arm having a reference lens, a mirror, means for adjusting the distance between the reference lens and the mirror and means for measuring the distance between the reference lens and the mirror; a test arm comprising a test lens; means for dividing the output of the source arm between the test arm and the reference arm; means for combining light reflected back into the reference arm and the test arm to create an interference signal; and means for detecting and analyzing the interference signal; fixing the test lens in place with respect to the container with the test lens aimed through the container toward the bottom of the container; establishing a baseline optical path distance for light reflecting off of the bottom of the empty container by manipulating the distance between the reference lens and the mirror until the maximum interference signal is detected and assigning a value of $X_0$ to the distance between the reference lens and the mirror in that position; placing the liquid in the container or allowing the liquid to accumulate in the container; establishing the optical path distance for light reflecting directly back from the bottom of the container by manipulating the distance between the reference lens and the mirror until the first strong maximum interference signal is detected and assigning a value of $X_1$ to the distance between the reference lens and the mirror in that position; establishing the optical path distance for light reflecting from the bottom of the container after being reflected from the bottom of the top of the liquid by manipulating the distance between the reference lens and the mirror until the second weak maximum interference signal is detected and assigning a value of $X_2$ to the distance between the reference lens and the mirror in that position; and establishing the following relationships:

i. $\Delta X_1 = X_1 - X_0$
ii. $\Delta X_2 = X_2 - X_0$;
iii. $\Delta X_1 = t \cdot n - t$; and
iv. $\Delta X_2 = 2t \cdot n - t$; and solving the system of equations to determine the thickness t and refractive index n of the liquid in the container.

DETAILED DESCRIPTION OF THE INVENTION

Figure 1:
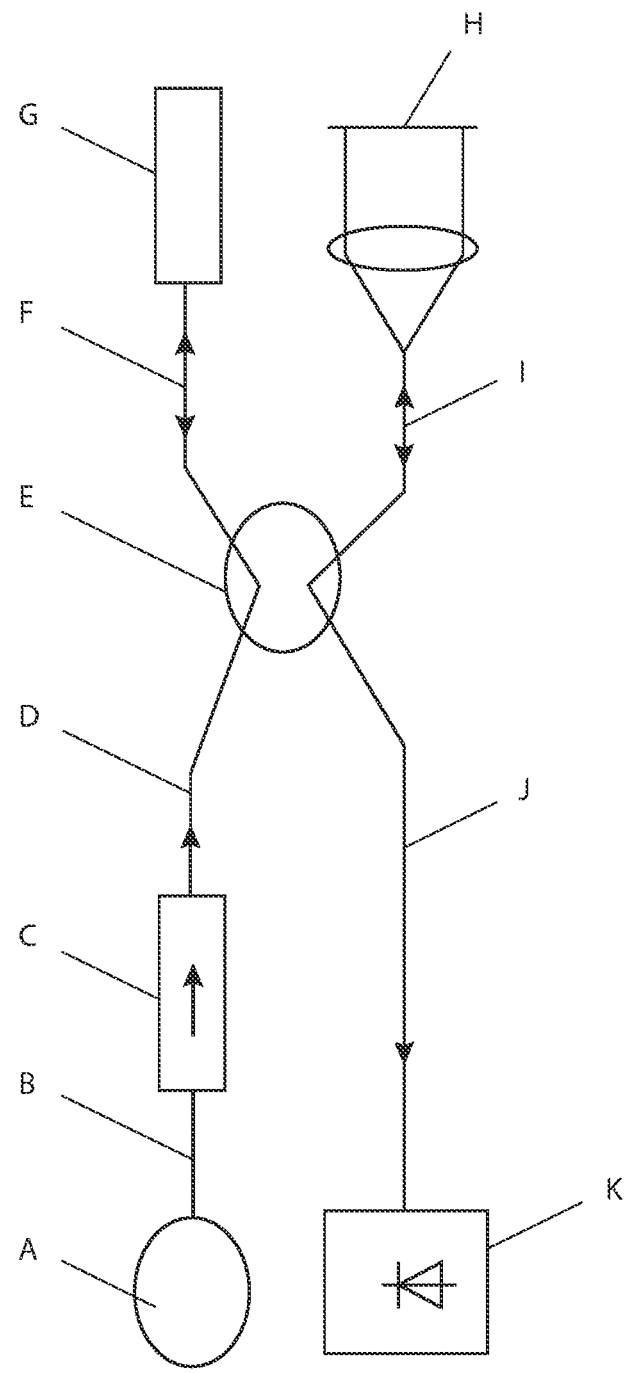
FIG. 1 is a block diagram depicting a prior art optical low coherence reflectometry system.
Figure 2:
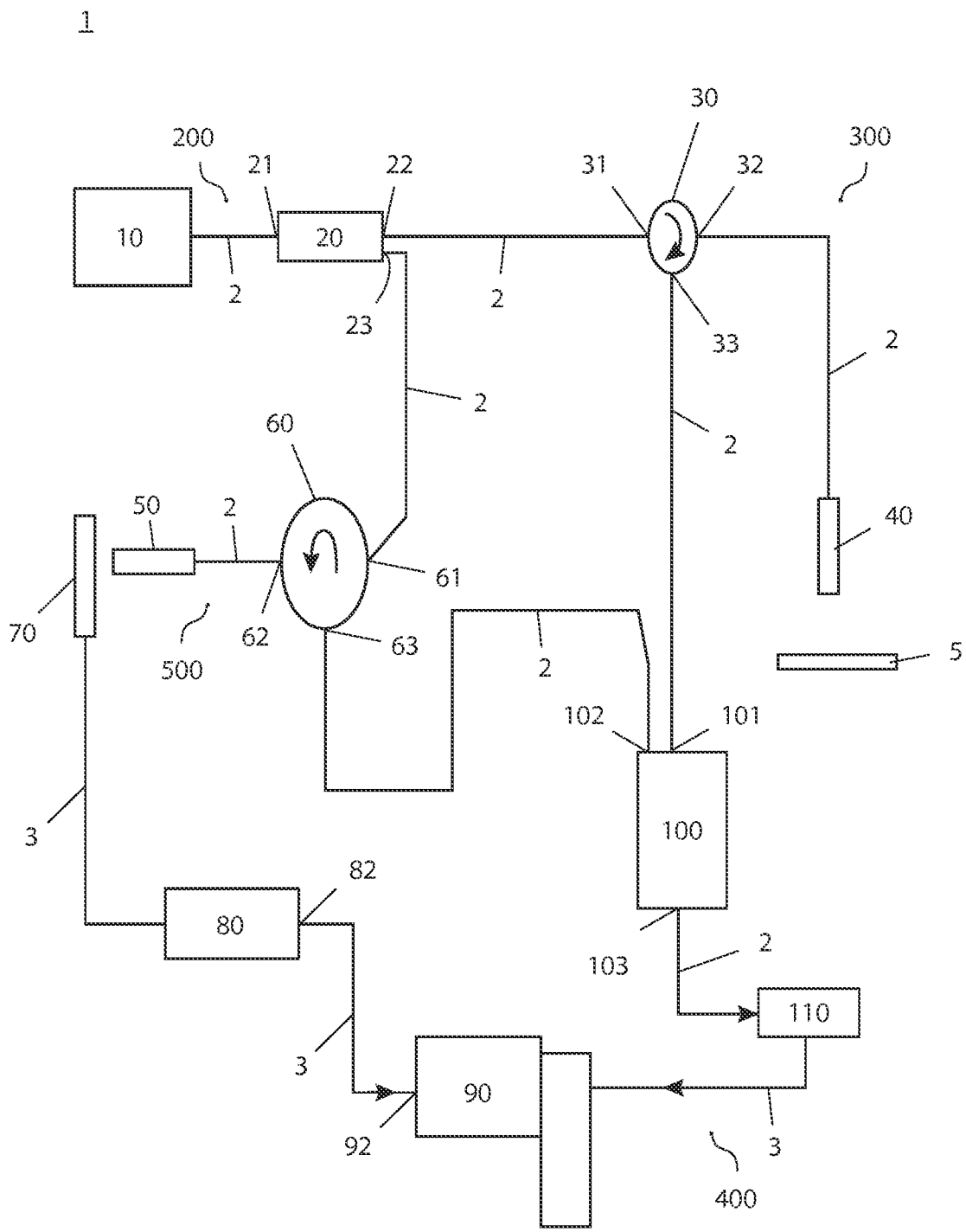
FIG. 2 is a block diagram depicting one embodiment of an apparatus for measuring the quantity and optical parameters of a liquid in a container using the principle of optical low coherence reflectometry.

Referring to FIG. 2, an embodiment of an apparatus for measuring the quantity and optical parameters of a liquid in a container using the principle of optical low coherence reflectometry is shown. Broadly stated system 1 includes source arm 200, test arm 300, receiver arm 400 and reference arm 500. More particularly, in this embodiment, measurement system 1 includes: fibers 2; wires 3; low coherence source 10; splitter 20 having input 21, first output 22 and second output 23; first circulator 30 having first port 31, second port 32 and third port 33; test lens 40; reference lens 50; second circulator 60 having first port 61, second port 62 and third port 63; moveable or oscillating mirror 70; function generator 80 having triggering output 82; oscilloscope 90 having triggering input 92; coupler 100 having first input 101, second input 102 and output 103; and interference signal detector 110.

In some embodiments, in operation, light from low coherence source 10 can pass through fiber 2 and enter splitter 20 through input 21. Splitter 20 distributes 98% of the source light to first port 31 of first circulator 30 through fiber 2. The light entering first port 31 of first circulator 30 passes through first circulator 30 to second port 32, then to test lens 40 through fiber 2. This light travels through test lens 40 to target 5 and reflects off target 5 back into test lens 40, then returns to second port 32 of first circulator 30 through fiber 2. The light entering second port 32 of first circulator 30 passes through first circulator 30 to third port 33, then to first input 101 of coupler 100 through fiber 2. Splitter 20 distributes the remaining 2% of the source light to first port 61 of second circulator 60 through fiber 2. The light entering first port 61 of second circulator 60 passes through second circulator 60 to second port 62, then to reference lens 50 through fiber 2. This light travels through reference lens 50 to oscillating mirror 70 and reflects off oscillating mirror 70 back into reference lens 50, then returns to second port 62 of second circulator 60 through fiber 2. The light entering second port 62 of second circulator 60 passes through second circulator 60 to third port 63, then to second input 102 of coupler 100 through fiber 2. Coupler 100 recombines the light entering first input 101 and the light entering second input 102 and to create an interference light signal, which exits coupler 100 through output 103 and travels to interference signal detector 110 through fiber 2. Interference signal detector 110 transmits an electric signal to oscilloscope 90 through wire 3. Oscilloscope 90 displays the signal, which allows the user to identify the positions of oscillating mirror 70 corresponding to interference maxima.

In some embodiments, in operation, function generator 80 can send a signal to oscillating mirror 70 through wire 3 to control the oscillation of oscillating mirror 70. Triggering output 82 of function generator 80 can be connected to triggering input 92 of oscilloscope 90 to allow oscilloscope 90 to accurately capture the electrical signal transmitted by interference signal detector 110 through wire 3.

Figure 3:
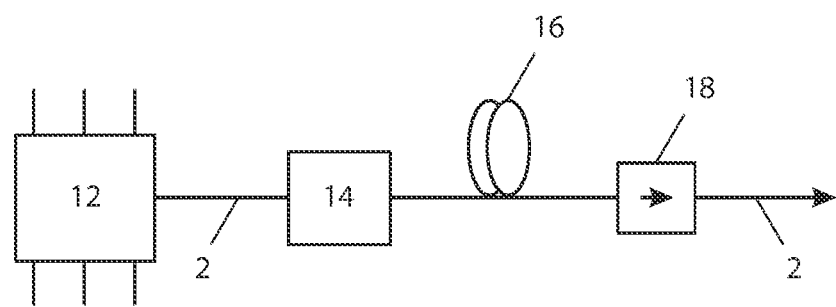
FIG. 3 is a block diagram depicting one embodiment of a low coherence source.

Referring to FIG. 3, one embodiment of low coherence source 10 is shown. Low coherence source 10 may include: laser diode 12; fibers 2; wavelength-division multiplexer 14; Erbium-doped fiber 16; and isolator 18. Laser diode 12 supplies light to wavelength-division multiplexer 14 and Erbium-doped fiber 16 through fiber 2. Wavelength-division multiplexer 14 and Erbium-doped fiber 16 amplify the light, and the amplified spontaneous emission output light passes through isolator 18 into fiber 2, which can connect to measurement system 10. Isolator 18 prevents feedback from measurement system 10 from passing through.

Figure 4:
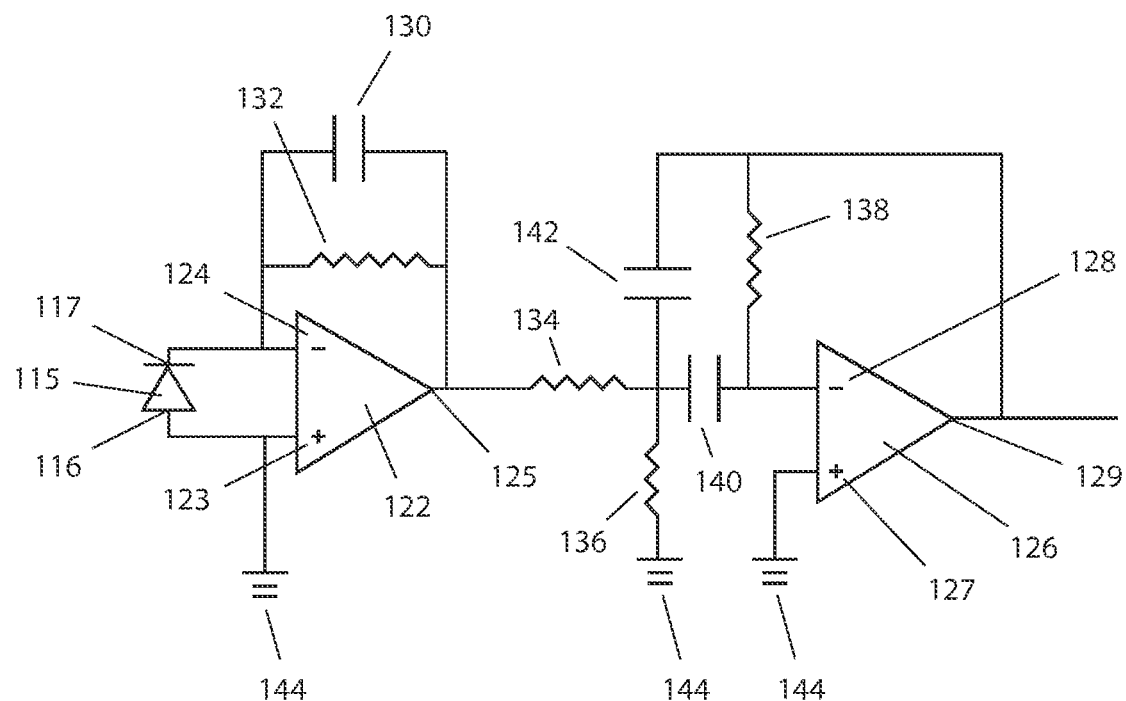
FIG. 4 is a schematic diagram depicting one embodiment of an interference signal detector.

Referring to FIG. 4, one embodiment of an interference signal detector 110 is shown. Interference signal detector 110 may include: photodiode 115 having first end 116 and second end 117; first operational amplifier 122 having positive input 123, negative input 124 and output 125; second operational amplifier 126 having positive input 127, negative input 128 and output 129; 10 pF capacitor 130; 300 kΩ resistor 132; 390 kΩ resistor 134; 1 kΩ resistor 136; 100 kΩ resistor 138; 10 nF capacitor 140; 330 pF capacitor 142; and circuit ground 144. Together, these components act to amplify the signal produced by photodiode 115 to provide an amplified output signal at output 129 of second operational amplifier 126. This amplified signal can then be captured and analyzed in order to locate the interference maxima.

Figure 5:
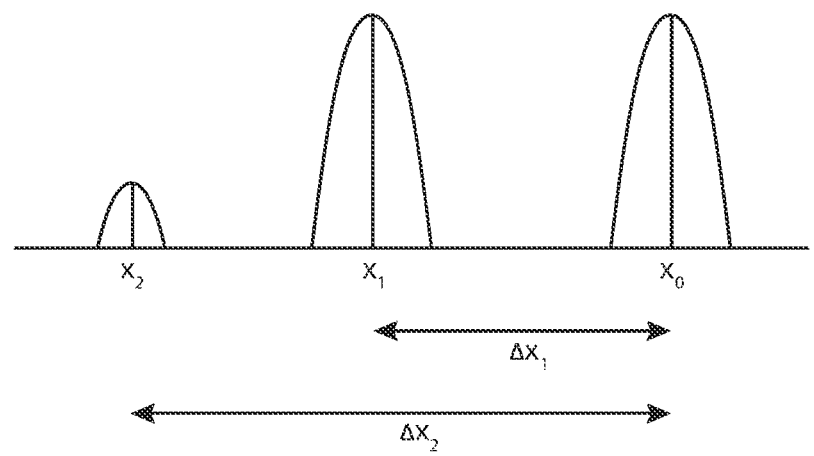
FIG. 5 is an X-Y graph depicting an interference pattern after adding liquid into a glass cylinder.

With respect to the methods and apparatuses used to demonstrate the embodiments disclosed above, various solid and liquid targets were tested with the OLCR measurement system by putting them in front of the test arm 300 and scanning the reference arm 500 to locate the maximum interference signal. Foam polyethylene was used as a solid target to represent a non-uniform medium with phase boundaries. In the case of foam polyethylene multiple interference, maxima that corresponded to the boundaries of the foam cells could be observed. In the case of liquids, simultaneous measurements of physical thickness and refractive index were carried out. For these studies, three liquids i.e. Hexane, Chloroform and diluted crude oil were used. These measurements were first done in the visible glass cylinder, and then in a high pressure cell. During these measurements, first, the position of the interference maxima for the empty cylinder was determined, and then with the addition of liquid the corresponding change in the maximum interference signal was recorded. Two maxima were observed after adding the liquid into the cylinder, and one maximum is found stronger in comparison of other maxima as illustrated in FIG. 5. As shown in FIG. 5, $X_0$ is the position of interference maximum without any liquid in the cylinder; $X_1$ is the position of maximum when liquid was added and $X_2$ is the position of second maximum.

Figure 6:
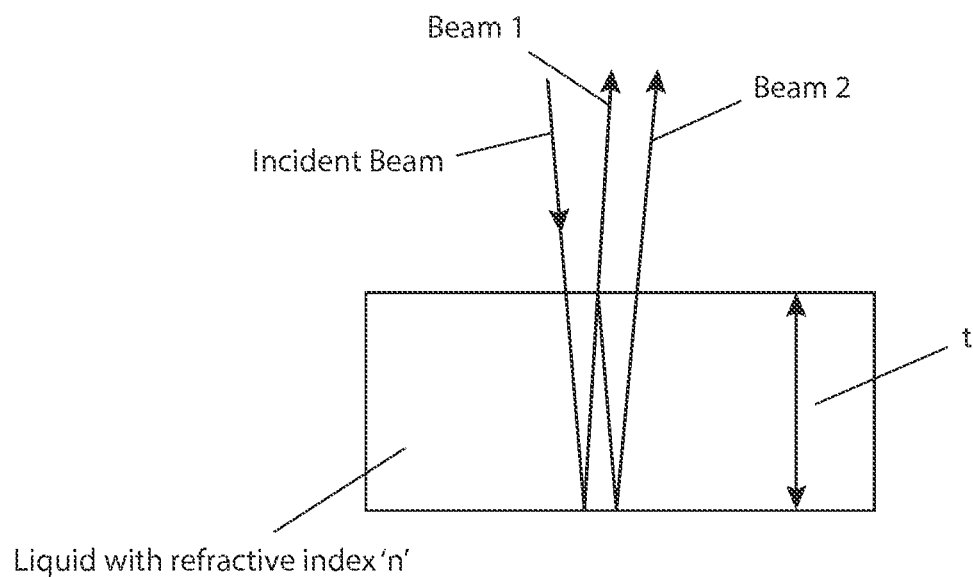
FIG. 6 is a side elevation view depicting two reflected beams of an incident beam directed into a volume of liquid.

Referring to FIG. 6, reflections from the bottom of the liquid with refractive index n and thickness t are shown. Beam 1 is the scattered beam from the surface at the bottom of the liquid, whereas Beam 2 is the doubly scattered beam from the bottom of the top surface of the liquid.

As shown in FIG. 6, the first strong maximum is the reflection from the bottom of the liquid in the cylinder. The second weak maximum is the double reflection from the bottom surface of the cell of light reflected from the bottom of the liquid layer. In case of clear liquid, no reflection was observed reflected directly from the top surface of the liquid since the alignment was not adjusted perfectly perpendicular to this layer.

Referring to FIG. 6, the extra optical path traveled by beam 1 is given as $$\Delta X_1 = t \cdot n - t \quad (5.1)$$

And for beam 2 it is given as $$\Delta X_2 = 2t \cdot n - t \quad (5.2)$$

Where 't' is the thickness and 'n' is the refractive index of the liquid. $\Delta X_1$ and $\Delta X_2$ are the total extra path lengths. So from the equations 5.1 and 5.2 we have two unknown parameters n and t and by solving these two equations algebraically we get the refractive index and the thickness of the liquid samples as given below:

$$t = \Delta X_2 - 2\Delta X_1 \quad (5.3)$$

$$n = \frac{\Delta X_2 - \Delta X_1}{\Delta X_2 - 2\Delta X_1} == 1 + \frac{\Delta X_1}{\Delta X_2 - 2\Delta X_1} \quad (5.4)$$

With the help of these equations, measurements of the liquid parameters in the glass cylinder and the blind test cell were carried out. Due to the physical construction of the glass cylinder and the blind test cell, they may have some meniscus on the liquid layer and some extra liquid is used to fill in small gaps in the bottom surface before getting the correct results. The amount of this extra liquid is called blind volume, and may also be calculated. The test experiments were performed with different liquids and the thickness and refractive index were calculated for these liquids.

A key advantage to the apparatus and method of the invention is the diffuse reflection from the bottom surface which takes advantage of the fact that the interferometric detection is very sensitive to weak reflected signals and, thus, in some embodiments, only a tiny return signal is required for the detection to work. In some embodiments, there is no requirement for precise alignment of the test beam in order to receive the back reflected signals directly into the collection lens. In one example application (a high pressure test cell), the measurement system can be inserted through a narrow opening (1-3 mm in diameter maximum due to the extremely high pressures up to 30,000 psi) in the top of the high pressure test cell. A fibre coupled source plus GRIN lens can be inserted through such an opening. If one had to align the back reflected light directly into the tiny 1 mm diameter GRIN lens after the propagation length of 30 cm to the bottom of the test cell, an accurate optical alignment system would be required which is totally incompatible with the very rough (high temperature, high pressure and high vibration—solutions are mixed physically by shaking) environment in which the tests are carried out. Thus, by using diffuse scattered light, in some embodiments, backscattered signals can be received without precise alignment.

In some conditions, the diffuse reflecting surface can have just the right amount of scattering to diffuse the light into a relatively narrow cone angle, for example, approximately 5 degrees so that the light will not be totally dispersed, and the signals not too weak. This can be particularly true for the signal reflected from the top surface of the liquid, which is scattered once from the bottom to the liquid surface and scattered again from the surface back to the detector. In some embodiments, unpolished machined metal surfaces work fairly well in this regard.

In some embodiments, the downward scattered signal from the liquid surface can be used for the measurement rather that the direct reflected signal from the liquid surface directly back into the detector that other measurement systems would use.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

What is claimed:

1. A method for calculating a thickness t and a refractive index n of a liquid in a container, the method comprising:
   providing an apparatus for measuring a quantity and optical parameters of the liquid in the container using optical low coherence reflectometry, the apparatus comprising:
   a source arm comprising a low coherence light source;
   a reference arm comprising a reference lens and a mirror, wherein a distance between the reference lens and the mirror is adjustable and measurable;
   a test arm comprising a test lens;
   a splitter for dividing an output of the source arm between the test arm and the reference arm;
   a coupler for combining light reflected back into the reference arm and the test arm to create an interference signal; and
   a device for detecting and analyzing the interference signal;
   fixing the test lens in place with respect to the container with the test lens aimed through the container;
   establishing a baseline optical path distance for light reflecting off of the container in an empty state by adjusting the distance between the reference lens and the mirror until a maximum interference signal is detected and determining a distance ($X_0$) between the reference lens and the mirror providing the maximum interference signal with the container in an empty state;
   placing the liquid in the container or allowing the liquid to accumulate in the container;
   establishing a first optical path distance for light reflecting directly back from the container by adjusting the distance between the reference lens and the mirror until a first strong maximum interference signal is detected and determining a distance ($X_1$) between the reference lens and the mirror providing the first strong maximum interference signal;
   establishing a second optical path distance for light reflecting from the container after being passed through the liquid by adjusting the distance between the reference lens and the mirror until a second weak maximum interference signal is detected and determining a distance ($X_2$) between the reference lens and the mirror providing the second weak maximum interference signal;
   determining a difference ($\Delta X_1$) between the distance ($X_1$) between the reference lens and the mirror providing the first strong maximum interference signal and the distance ($X_0$) between the reference lens and the mirror providing the maximum interference signal with the container in an empty state;
   determining a difference ($\Delta X_2$) between the distance ($X_2$) between the reference lens and the mirror providing the second weak maximum interference signal and the distance ($X_0$) between the reference lens and the mirror providing the maximum interference signal with the container in an empty state; and
   solving equations $\Delta X_1 = t \cdot n - t$ and $\Delta X_2 = 2t \cdot n - t$ to determine the thickness t and the refractive index n of the liquid in the container.

2. The method as set forth in claim 1 wherein the source arm further comprises an isolator to prevent feedback from the reference arm and the test arm from entering the source arm.

3. The method as set forth in claim 1 wherein the low coherence light source further comprises an Erbium-doped fiber amplifier.

4. The method as set forth in claim 1 wherein the reference arm further comprises a phase modulator.

5. The method in claim 4 wherein the phase modulator comprises a function generator and the mirror is configured to be oscillated in accordance with the output of the function generator, with the function generator used to trigger the device for detecting and analyzing the interference signal.

6. The method as set forth in claim 1 wherein the test lens is a gradient-index lens.

7. The method as set forth in claim 1 wherein the device for detecting and analyzing the interference signal comprise a photodiode, an operational amplifier circuit, an analog-to-digital converter, and a computer.

8. The method as set forth in claim 1 wherein the source arm, the reference arm, the test arm, the splitter and the coupler comprise fiber optic components.

* * * * *